US011434144B2

(12) United States Patent
Lebrun

(10) Patent No.: US 11,434,144 B2
(45) Date of Patent: Sep. 6, 2022

(54) DURABLE POWDER COMPOSITION

(71) Applicant: SOCIETE INDUSTRIELLE LIEGEOISE DES OXYDES SA, Engis (BE)

(72) Inventor: Benoît Lebrun, Milmort (BE)

(73) Assignee: SOCIETE INDUSTRIELLE LIEGEOISE DES OXYDES SA, Engis (BE)

(*) Notice: Subject to any disclaimer, the term of this patent is extended or adjusted under 35 U.S.C. 154(b) by 114 days.

(21) Appl. No.: 16/468,132

(22) PCT Filed: Dec. 14, 2017

(86) PCT No.: PCT/EP2017/082899
§ 371 (c)(1),
(2) Date: Jun. 10, 2019

(87) PCT Pub. No.: WO2018/109113
PCT Pub. Date: Jun. 21, 2018

(65) Prior Publication Data
US 2020/0071182 A1  Mar. 5, 2020

(30) Foreign Application Priority Data
Dec. 16, 2016 (BE) .................................. 2016/5939

(51) Int. Cl.
| | |
|---|---|
| *C01G 9/02* | (2006.01) |
| *A23K 20/24* | (2016.01) |
| *A23K 20/20* | (2016.01) |
| *A61K 8/19* | (2006.01) |
| *A61K 8/27* | (2006.01) |
| *C05D 9/02* | (2006.01) |
| *C08C 19/20* | (2006.01) |
| *C08L 23/16* | (2006.01) |
| *C09C 1/04* | (2006.01) |

(52) U.S. Cl.
CPC ............... *C01G 9/02* (2013.01); *A23K 20/24* (2016.05); *A23K 20/30* (2016.05); *A61K 8/19* (2013.01); *A61K 8/27* (2013.01); *C05D 9/02* (2013.01); *C08C 19/20* (2013.01); *C08L 23/16* (2013.01); *C09C 1/043* (2013.01); *C01P 2004/51* (2013.01); *C01P 2004/61* (2013.01); *C01P 2004/62* (2013.01); *C01P 2004/82* (2013.01); *C01P 2006/12* (2013.01); *C08L 2205/025* (2013.01); *C08L 2312/00* (2013.01)

(58) Field of Classification Search
None
See application file for complete search history.

(56) References Cited

U.S. PATENT DOCUMENTS 4,222,915 A * 9/1980 Wolff .................. C08K 5/5406
524/574
6,057,395 A * 5/2000 Nishimura ............... C08K 3/20
524/397

FOREIGN PATENT DOCUMENTS

| CN | 102312193 A | 1/2012 | |
|---|---|---|---|
| CN | 106380193 A * | 2/2017 | ........... C04B 35/453 |
| WO | 2010094764 A1 | 8/2010 | |

OTHER PUBLICATIONS

Osamu Yamamoto, Change in antibacterial characteristics with doping amount of ZnO in MgO—ZnO solid solution, 2000, International Journal of Inorganic Materials, vol. 2, pp. 451-454 (Year: 2000).*
International Search Report dated Feb. 27, 2018, issued in corresponding International Application No. PCT/EP2017/082899, filed Dec. 14, 2017, 7 pages.
Written Opinion of the International Searching Authority dated Feb. 27, 2018, issued in corresponding International Application No. PCT/EP2017/082899, filed Dec. 14, 2017, 5 pages.
Ohira, T. et al., "Influence of the Mixing Ratio on Antibacterial Characteristics of MgO—ZnO Solid Solution in Two Phase Coexistence Region," 2008, The Ceramic Society of Japan Journal of the Ceramic Society of Japan, 116(11):1234-1237, Nov. 2008.
Guzman, M. et al., "Zinc Oxide Versus Magnesium Oxide Revisited. Part 1," Rubber Chemistry and Techology American Chemical Society USA, vol. 85, No. 1, Mar. 2012, pp. 38-55.
Written Opinion of the International Searching Authority dated Feb. 27, 2018, issued in corresponding International Application No. PCT/EP2017/082899, filed Dec. 14, 2017, 6 pages.
International Preliminary Report on Patentability dated Jun. 18, 2019, issued in corresponding International Application No. PCT/EP2017/082899, filed Dec. 14, 2017, 1 page.

* cited by examiner

*Primary Examiner* — Nannette Holloman
(74) *Attorney, Agent, or Firm* — Christensen O'Connor Johnson Kindness

(57) ABSTRACT

The present invention relates to a detoxified powder composition comprising a zinc-bearing compound selected from the group consisting of zinc carbonate, zinc hydroxide, zinc oxide, zinc sulphate and mixtures thereof, and at least one detoxification agent containing at least one oxide based on a cation, selected from the group consisting of calcium, barium, magnesium, strontium and beryllium.

8 Claims, No Drawings

DURABLE POWDER COMPOSITION

The present invention relates to a detoxified powder composition comprising a zinc-bearing compound and at least one detoxification agent, the production method thereof and the uses thereof.

It is known that zinc-bearing compounds are considered as being highly toxic substances for aquatic organisms, which leads to long-term harmful effects on the environment. Indeed, this observation is moreover described in European regulation (EC) no. 1272/2008 of the European Parliament and Council of 16 Dec. 2008 relating to the classification, labelling and packaging of the substances and the mixtures, modifying and amending directives 67/548/EEC and 1999/45/EC, and furthermore modifying the regulation (EC) no. 1907/2006. This European regulation makes it possible to inform individuals regarding the risks linked to the uses of chemical substances.

More specifically, the aim of the abovementioned European regulation makes it possible, to some extent, to inform individuals of the toxicity of chemical substances in order to be able to implement a suitable classification, labelling and packaging system for users of such substances. This ultimately makes it possible, to ensure a free circulation of goods, in a sufficiently controlled and notified manner, in particular in the European Union.

Unfortunately, the integration of such a system is more and more constraining for the user, given that the classification, labelling and packaging criteria become more and more strict. In addition, respecting and applying this regulation generates non negligible costs for the user, without considering that this system can vary for countries located outside of the European Union, which makes classification, labelling and packaging all the more complex.

Certain users have decided to reduce, as much as possible, the use of such chemical substances, even completely remove the uses thereof to attempt to avoid having to reduce their margin linked to the sale of these products on the market.

For this reason, using these zinc-bearing compounds can be reduced to a few fields of application, which does not make it possible to sufficiently enhance these products, considered as being harmful to the environment.

Therefore, there is a real need to provide a detoxified powder composition and this, despite the presence of a zinc-bearing compound, so as to be able to benefit from the physico-chemical properties of said zinc-bearing compound in various fields of application, in particular in the vulcanising of rubber, preferably synthetic or natural.

In this context, the aim sought in the scope of the present invention is to provide a detoxified powder composition which is durable, exempt of aquatic ecotoxicity and which can be valorized in various fields of application.

To resolve this problem, a detoxified powder composition is provided, according to the invention, comprising a zinc-bearing compound selected from the group consisting of zinc carbonate, zinc hydroxide, zinc oxide, zinc sulphate and mixtures thereof, and at least one detoxification agent containing at least one oxide based on a cation selected from the group consisting of calcium, barium, magnesium, strontium and beryllium.

It has been observed, that the zinc-bearing compound, selected from the group consisting of zinc carbonate, zinc hydroxide, zinc oxide, zinc sulphate and mixtures thereof, is an ideal candidate for numerous uses, in particular in the context of formulations of vulcanising agent for rubber, preferably synthetic or natural.

In addition, the specific combination of the zinc-bearing compound, selected from the group consisting of zinc carbonate, zinc hydroxide, zinc oxide, zinc sulphate and mixtures thereof, and the detoxification agent, preferably in a solid form, makes it possible to provide a composition ready for use in various fields of use.

Preferably, the zinc-bearing compound is in a solid form.

More specifically, the composition according to the invention can be used in a formulation intended to provide a vulcanising agent for rubber, preferably synthetic or natural. This can also be used to obtain adhesives, lubricants, fertilising substances, anti-ultraviolet compounds for plastics and cosmetic materials or substances for animal food and anticorrosion paints.

Moreover, it has been observed, that the composition used as a vulcanising agent does not alter the characteristics of the rubber thus obtained.

Advantageously, said detoxified powder composition according to the present invention presents an algae inhibition rate less than 50%, according to the OECD 201 protocol, a *Daphnia* immobilisation rate less than 50% according to the OECD 202 protocol, a fish mortality rate less than 50% according to the OECD 203 protocol, which leads to CL50 (lethal concentration by ingestion for 50% of the population) and CE50 (lethal concentration by inhalation for 50% of the population) greater than 100 mg/l, and an NOEC (no observed effect concentration) strictly greater than 1 mg/l on the reproduction of *Daphnia* according to the OECD 211 protocol.

Preferably, said composition according to the invention has a particle size $d_{50}$ comprised within a range from 0.5 to 20 µm, preferably from 1 to 10 µm, more preferably from 3 to 5 µm, measured by laser granulometry with ultrasounds, where the dispersant is water.

More preferably, said composition according to the invention has a particle size $d_{10}$ from 0.1 to 5 µm, preferably from 0.5 to 1.5 µm, even more preferably from 0.7 to 0.9 µm.

Preferably, said composition according to the invention has a particle size $d_{90}$ from 2 to 50 µm, preferably from 5 to 20 µm, more preferably from 10 to 15 µm.

Even more preferably, said composition according to the invention has a particle size $d_{97}$ from 5 to 200 µm, preferably from 20 to 40 µm, even more preferably from 25 to 35 µm.

According to a preferred embodiment, the composition according to the invention has a specific surface area less than 80 m²/g, preferably less than 65 m²/g, more preferably between 40 and 60 m²/g, even more preferably between 40 and 50 m²/g, advantageously less than 40 m²/g, even more advantageously between 3 and 10 m²/g, measured by physical adsorption according to the B.E.T method (Brunauer-Emmett-Taylor/gas is an $N_2$ and $H_2$ mixture).

Advantageously, said zinc-bearing compound is zinc oxide and the detoxification agent is magnesium oxide. This composition can thus have a specific surface area from 40 to 60 m²/g, preferably from 40 to 50 m²/g, measured by physical adsorption according to the B.E.T method (Brunauer-Emmett-Taylor/gas is an $N_2$ and $H_2$ mixture). Such a composition can preferably be used in the vulcanization of rubber.

The magnesium oxide can have a distribution of average particle sizes from 6 to 10 µm, preferably from 7 to 8 µm, advantageously measured by laser granulometry with ultrasounds, where the dispersant is water.

Preferably, the detoxification agent is magnesium oxide. More preferably, the zinc-bearing compound is zinc oxide.

According to a specific embodiment, the composition according to the invention comprises between 92.5 and 99.5% by weight, preferably between 93 and 97% by weight, more preferably between 95 and 96% by weight of said zinc-bearing compound, and between 0.5 and 7.5% by weight, preferably between 3.5 and 7.5% by weight, more preferably between 4 and 5% by weight of magnesium oxide with respect to the total weight of the composition.

Indeed, advantageously, the composition according to the invention can comprise around 93% by weight of zinc oxide and around 7% by weight of magnesium oxide, with respect to the total weight of the composition.

Preferably, the composition according to the invention can comprise between 97 and 99% by weight of zinc oxide or around 99% by weight of zinc oxide and between 1 and 3% by weight of magnesium oxide or 1% by weight of magnesium oxide, determined with respect to the total weight of the composition. Such a composition can contain a vulcanising agent, particularly effective in producing rubber.

In the scope of the present invention, the composition can be formed by said zinc-bearing compound and said magnesium oxide. This composition does not exclude the presence of impurities in the mixture or of inactive elements in that they only act slightly, or even not at all, on the physico-chemical characteristics of the composition according to the invention. For this reason, the term "around" is used to reflect the presence of possible impurities or any other inactive elements in the final composition.

Preferably, the composition according to the invention is a vulcanising agent of rubber, preferably synthetic or natural.

Other embodiments of the composition according to the invention are indicated in the appended claims.

The present invention also relates to a vulcanising agent comprising the composition according to the invention.

Other embodiments of the vulcanising agent according to the invention are indicated in the appended claims.

The present invention also relates to a composition of adhesives comprising the composition according to the invention.

Other embodiments of the composition of adhesives according to the invention are indicated in the appended claims.

The present invention also relates to a fertiliser comprising the composition according to the invention.

Other embodiments of the fertiliser according to the invention are indicated in the appended claims.

The present invention also relates to anti-ultraviolet compounds for plastic and cosmetic materials comprising the composition according to the invention.

Other embodiments of the anti-ultraviolet compound for plastic and cosmetic materials according to the invention are indicated in the appended claims.

The present invention relates to a substance for animal food comprising the composition according to the invention.

Other embodiments of the substance for animal food according to the invention are indicated in the appended claims.

The present invention also relates to a detoxified composition, and preferably micronised, which comprises a zinc-bearing compound selected from the group consisting of zinc carbonate, zinc hydroxide, zinc oxide, zinc sulphate and mixtures thereof, and at least one detoxification agent containing at least one oxide based on a cation selected from the group consisting of calcium, barium, magnesium, strontium and beryllium, said composition having a specific surface area greater than 30 m$^2$/g, measured by physical adsorption according to the B.E.T method (Brunauer-Emmett-Taylor/gas is an $N_2$ and $H_2$ mixture).

Other embodiments of the detoxified composition are indicated in the appended claims.

The invention also relates to a method for producing a detoxified powder composition comprising a solid-solid mixture of a zinc-bearing compound selected from the group consisting of zinc carbonate, zinc hydroxide, zinc oxide, zinc sulphate and mixtures thereof, and a detoxification agent containing at least one oxide based on a cation selected from the group consisting of calcium, barium, magnesium strontium and beryllium to provide the detoxified powder composition.

Particularly advantageously, said zinc-bearing compound, in particular zinc oxide, is obtained by wet processes. Zinc oxide can thus have a nodular morphology.

According to a preferred embodiment, said composition according to the invention has a particle size $d_{50}$ comprised within a range from 0.5 to 20 µm, preferably from 1 to 10 µm, more preferably from 3 to 5 µm, measured by laser granulometry with ultrasounds, where the dispersant is water, for example with an instrument from the brand Malvern.

Advantageously, said composition according to the invention has a particle size $d_{10}$ from 0.1 to 5 µm, preferably from 0.5 to 1.5 µm, even more preferably from 0.7 to 0.9 µm.

Preferably, said composition according to the invention has a particle size $d_{90}$ from 2 to 50 µm, preferably from 5 to 20 µm, even more preferably going from 10 to 15 µm.

Even more preferably, said composition according to the invention has a particle size $d_{97}$ from 5 to 200 µm, preferably from 20 to 40 µm, even more preferably from 25 to 35 µm.

Advantageously, said zinc-bearing compound is zinc oxide and the detoxification agent is magnesium oxide.

The magnesium oxide can have a distribution of average particle sizes from 6 to 10 µm, preferably from 7 to 9 µm, where $d_{50}$ is measured by laser granulometry with ultrasounds, where the dispersant is water.

According to a specific production method, the composition according to the invention comprises zinc oxide and magnesium oxide.

The method according to the invention can also be characterised by one or more of the characteristics mentioned for the composition, such as indicated above.

Other embodiments of the method according to the invention are indicated in the appended claims.

The invention also has as an object the use of the composition according to the invention or obtained according to the production method according to the invention, as a rubber vulcanising agent, in obtaining adhesives, lubricants, fertilising substances, anti-ultraviolet compounds for plastics and cosmetic materials, substances for animal food, anticorrosion paints.

Other embodiments of the use according to the invention are indicated in the appended claims.

Other characteristics, details and advantages of the invention will emerge from the description given below, in a non-limiting manner and by making reference to the appended drawings.

In the present invention, the notation $d_x$ (for example, $d_{50}$) represents the diameter (expressed in µm) of the particles with respect to which x % (for example, 50%) of the particles measured from the distribution are of a smaller size.

In the context of the present invention, "phr" is a unit of measurement which makes it possible to express the number of zinc oxide parts with respect to the number of rubber parts expressed by weight. Therefore, one phr of zinc oxide is the equivalent, on the one hand, of zinc oxide for 100 parts of rubber, expressed by weight.

In the context of the present invention, the terms "comprising", "comprises" can be replaced by the terms "containing" or "consisting of" or "consists of" in order to limit the composition to the elements that it contains. It is understood that the composition can also be limited by any of the characteristics mentioned in the present patent application.

The composition according to the invention can thus comprise or be constituted of zinc oxide and magnesium oxide. This does not exclude the presence of impurities or elements present in lesser quantities with respect to the zinc-bearing compound, like zinc oxide, and magnesium oxide. These abovementioned impurities or slightly-active elements, or inactive on the physico-chemical characteristics of the composition according to the invention. This composition will be particularly preferred in the scope of the present invention.

In the context of the present invention, the expression, "zinc-bearing compound", means a compound containing zinc, where the zinc acts on the physico-chemical characteristics of the composition. In other words, if the zinc-bearing compound is zinc oxide, this contributes actively to the vulcanising when it contains a vulcanising agent for rubber.

Similarly, in the context of the present invention, the term, "detoxification agent", means a compound where the oxide considered according to the invention, for example magnesium oxide, acts actively on the physico-chemical characteristics of the composition.

The method for producing the detoxified powder composition according to the present invention can comprise a solid-solid mixture of a zinc-bearing compound, preferably zinc oxide and a detoxification agent containing at least one oxide based on a cation selected from the group consisting of calcium, barium, magnesium, strontium and beryllium, to provide the detoxified powder composition.

Preferably, the method according to the invention consists of mixing zinc oxide in a solid form with magnesium oxide in a solid form.

This production method thus makes it possible to provide a composition which can be used as a rubber vulcanising agent.

In the scope of the present invention, zinc oxide can be obtained thermally (that is, direct or indirect) or also by wet processes (precipitation), i.e. by converting complex zinc salts into zinc oxide having a nodular morphology.

According to a preferred embodiment, the zinc oxide advantageously has a nodular morphology.

Typically, a zinc oxide produced thermally (direct or indirect) makes it possible to obtain a zinc oxide having a specific surface area, measured by physical adsorption according to the B.E.T method (Brunauer-Emmett-Taylor), which is lesser with respect to a zinc oxide obtained by wet processes. Indeed, a zinc oxide obtained by wet processes will have a larger specific surface area, preferably greater than 30 $m^2/g$, given that the generated crystallography makes it possible.

However, it is possible to reduce this increased specific surface area to a value less than, for example, between 5 and 30 $m^2/g$. For this, a calcination step can be applied on the product obtained by wet processes, in order to reduce the specific surface area of the zinc oxide.

The modulation of the specific surface area of the zinc oxide therefore depends on the method applied upstream and possible additional steps later applied, like calcination or equivalent.

To obtain zinc oxide, as an example, chapters 2.17.1 and 2.17.2 of the European Commission report entitled, "Reference Document on Best Available Techniques for the Manufacture of Large Volume Inorganic Chemicals Solids and Others Industry" are referred to. This document and more specifically the abovementioned chapters are incorporated by reference in the present patent application to describe the abovementioned thermal and wet processes.

The document is accessible on the following internet link: http://eppcb.jrc.ec.europa.eu/reference/BREF/lvic-s_bref_0907.pdf.

The composition according to the invention can be used in formulation or in formation of products for colouring/pigment, animal food, fuel, laboratory chemical substances, lubricants and additives, metallisation agent, industrial uses of process regulators for polymerisation processes in producing resins, rubber, polymers; battery, corrosion inhibitor, descaling agent, fertiliser, pharmaceutical industry, photochemical products, semiconductors, processing aids, additives for fuels, metal surface treatment products, including products for galvanisation and galvanoplasty.

According to a particularly advantageous embodiment, the composition according to the invention forms a vulcanising agent for rubber, preferably synthetic or natural.

The composition according to the invention has no ecotoxicity which makes it possible to avoid any specific labelling linked to the use of such a composition.

Typically, there are two methods for determining dangerous labelling for the environment of the preparations:

A first technique consists of applying the rule of the substance mixtures, i.e. considering the composition of the product. Thus, according to this technique, any product containing zinc is, due to this, dangerous for the environment.

A second technique is rather based on ecotoxicity test according to the OECD 201, 202, 203 protocols for acute ecotoxicity on the preparation containing dangerous materials.

According to regulations 1999/45/EC and 1272/2008/EC covering the classification criteria of a preparation or a mixture tested, containing at least one dangerous material, the abovementioned second technique takes precedence over the first.

Applying these protocols leads to considering tests on algae, *Daphnia* and fish.

From a regulation standpoint, it has been considered, from modified appendix 5 of directive 67/548/EEC, directive 99/45/EEC relative to the modified preparations, the GHS report produced in 2003-part 3, paragraph 3.10.3, relating to the classification criteria of mixtures, and tests have been carried out according to the guidelines of OECD 201 adopted on 23 Mar. 2006, 202 adopted on 13 Apr. 2004 and 203 adopted on 17 Jul. 1992.

Thus, according to the results obtained for each of the abovementioned tests, the conventional labelling of a compound can be carried out.

The table 1 below relates to the labelling and to the risk phrases according to the results obtained during ecotoxicity tests according to 1999/45/EC.

This table 1 illustrates, for each type of test, a concentration C expressed in mg/l, a test duration expressed in hours, a rate of 50% of species succumbing at the end of the number of hours considered, the corresponding labelling according to the concentration C indicated and the associated risk phrases.

TABLE 1

| Tests | Concentration C | Labelling | Risk phrase |
|---|---|---|---|
| 96 H CL50 (fish) 48 H CE50 (*daphnia*) 72 H CL50 (algae) | <1 mg/l | GHS09 Graphical Icon | R50/53 Highly toxic for aquatic organisms, can lead to long-term harmful effects for the aquatic environment |
| 96 H CL50 (fish) 48 H CE50 (*daphnia*) 72 H CL50 (algae) | Between 1 and 10 mg/l | GHS09 Graphical Icon | R51/53 Toxic for aquatic organisms, can lead to long-term harmful effects for the aquatic environment |
| 96 H CL50 (fish) 48 H CE50 (*daphnia*) 72 H CL50 (algae) | Between 10 and 100 mg/l | None | R52/53 Harmful for aquatic organisms, can lead to long-term harmful effects for the aquatic environment |
| 96 H CL50 (fish) 48 H CE50 (*daphnia*) 72 H CL50 (algae) | >100 mg/l | None | R53 or no risk phrase according to the chronic ecotoxicity |

The global harmonised labelling system GHS in its latest revision of 2009, reiterates and confirms the maximum limits of 1 mg/l for category 1, of 10 mg/l for category 2 (1 mg/l to 10 mg/l) and of 100 mg/l for category 3 (10 mg/l to 100 mg/l), as classification criteria of acute aquatic toxicity. Above 100 mg/l of acute toxicity, the substance or the preparation is not classified for the toxicity thereof. Between 10 and 100 mg/l, the use of the substance involves no specific labelling.

Furthermore, the GHS also specifies that when the chronic toxicity has no observed effect concentration greater than 1 mg/l, thus this substance or this mixture is not subjected to classification for the chronic character thereof.

Acute toxicity tests have been carried out by a centre approved in this regard. The preparation has been produced by physical mixture.

The term GLP means tests carried out according to Good Laboratory Practice.

The reference CL50 relates to the lethal concentration by ingestion for 50% of the population in question.

The reference CE50 relates to the lethal concentration by inhalation for 50% of the population.

The reference CI50 relates to the median inhibiting concentration to inhibit 50% of the population.

The reference ErC50 relates to the concentration producing 50% of effect over the growth rate.

EXAMPLE 1

A composition according to a first production method is obtained by mixing 99% by weight of zinc oxide with 1% by weight of magnesium oxide.

The acute ecotoxicity results on *Oncorhynchus mykiss* fish are illustrated in table 2, which illustrates that no trout had died. The preparation has no toxicity for fish, due to an acute ecotoxicity CE50>100 mg/L, according to the OECD 203 protocol, dated 17 Jul. 1992.

TABLE 2

| PREPARATION | GLP/NON-GPL TEST | NUMBER OF TROUT | TROUT MORTALITY | CE50 (MG/L) |
|---|---|---|---|---|
| ZA 99 | NON-GLP | 10 | 0 | >100 |

The acute ecotoxicity results on *Daphnia magna* crustaceans are illustrated in table 3 below, which illustrates that no *Daphnia* has been immobilised. The preparation therefore has no toxicity for crustaceans due to an acute ecotoxicity CE50>100 mg/L, according to the OECD 202 protocol, dated 13 Apr. 2004.

TABLE 3

| PREPARATION | GLP/NON-GLP TEST | DAPHNIA IMMOBILISATION | CE50 (MG/L) |
|---|---|---|---|
| ZA 99 | NON-GLP | 0 | >100 |

The acute ecotoxicity results on *Pseudokirchneriella subcapitata* algae are illustrated in table 4 below, which illustrates that the inhibition of algae is between 10 and 100 mg/l, according to the OECD 201 protocol, dated 23 Mar. 2006. Using this preparation does not therefore require any labelling on the packaging.

TABLE 4

| PREPARATION | GLP/NON-GLP TEST | CI50 (MG/L) |
|---|---|---|
| ZA 99 | NON-GLP | COMPRISED BETWEEN 10 AND 100 |

EXAMPLE 2

A composition according to a second embodiment has been obtained by mixing 99% by weight of zinc oxide with 1% by weight of magnesium oxide.

Table 5 illustrates the ecotoxicity results on fish, *Daphnia* and algae, respectively based on the OECD 203, OECD 202 and OECD 201 protocols.

In the three cases, the composition has no toxicity due to an acute ecotoxicity CE50 or CL50 or ErC50>100 mg/L.

TABLE 5

| Tests | Results |
|---|---|
| CL50 fish | >100 mg/l (96 hours) |
| CE50 daphnia | >100 mg/l (48 hours) |
| ErC50 (algae) | >100 mg/l (72 hours) |
| NOEC (chronic) | >1 mg/l (21 days) |

EXAMPLE 3

Example 3 relates to the formation of a rubber vulcanising agent by means of the composition according to the invention.

According to table 6, the following compounds are mixed: 75 phr of ethylene-propylene-diene monomer rubber (EPDM 9500), 25 phr ethylene-propylene-diene monomer (EPDM 2504), 2 phr stearic acid, 5 phr of the composition according to the invention, 0.5 phr of 2,2,4-Trimethyl-1,2-Dihydroquinoline (TMQ, antioxidant), 140 phr of a charge containing black carbon, 85 phr of paraffinic oil, 0.8 phr of 2-Mercaptobenzothiazole (MBT), 0.6 phr of zinc ethylene-bis-dithiocarbamate (ZEDC), 0.6 phr of zinc dibutyl-dithiocarbamate (ZBDC), 0.6 phr of dithiodimorpholine (DTDM) and 0.6 phr of sulphur. The 5 phrs of the composition according to the invention comprise around 99% by weight of ZnO and around 1% by weight of MgO (the remainder being formed by impurities or inactive elements in the composition). In other words, 4.95 phr of ZnO and 0.05 phr of MgO form the composition according to the invention.

TABLE 6

| Formulation | phr |
| --- | --- |
| EPDM 9500 | 75 |
| EPDM 2504 | 25 |
| Stearic acid | 2 |
| Composition according to the invention | 5 |
| TMQ | 0.5 |
| Black FEF 550 | 140 |
| Paraffinic Oil | 85 |
| MBT | 0.8 |
| ZEDC | 0.6 |
| ZBDC | 0.6 |
| DTDM | 0.6 |
| Sulphur | 0.6 |

It is understood that the present invention is, in no manner, limited to the embodiments described above and that modifications can be applied to them, without moving away from the scope of the appended claims.

The invention claimed is:

1. A detoxified powder composition suitable for use as a vulcanization agent for rubber, comprising a zinc-bearing compound selected from the group consisting of zinc carbonate, zinc hydroxide, zinc oxide, zinc sulphate and mixtures thereof, and at least one detoxification agent being magnesium oxide, wherein the composition comprises between 92.5 and 99.5% by weight of said zinc-bearing compound and between 0.5 and 7.5% by weight of magnesium oxide with respect to the total weight of the composition, wherein the composition has a specific surface area less than 80 $m^2/g$, and wherein the zinc-bearing compound has a specific surface area greater than 30 $m^2/g$, as measured by physical adsorption according to the B.E.T method (Brunauer-Emmett-Taylor).

2. The composition according to claim 1, wherein the composition has a particle size d50 comprised within a range from 0.5 to 20 μm, as measured by laser granulometry with ultrasounds, where the dispersant is water.

3. A vulcanizing agent comprising the composition according to claim 1.

4. A method for producing a detoxified powder composition, the method comprising:
    mixing between 92.5% and 99.5% by weight of a zinc-bearing compound selected from the group consisting of zinc carbonate, zinc hydroxide, zinc oxide, zinc sulphate and mixtures thereof, with between 0.5% and 7.5% by weight of magnesium oxide with respect to the total weight of the composition to provide the detoxified powder composition,
    wherein the composition has a specific surface area less than 80 $m^2/g$ and wherein the zinc-bearing compound has a specific surface area greater than 30 m2/g, as measured by physical adsorption according to the B.E.T method (Brunauer-Emmett-Taylor).

5. The method according to claim 4, wherein said zinc-bearing compound is zinc oxide obtained by wet processes which has a nodular morphology.

6. The method according to claim 4, wherein said composition has a particle size d50 comprised within a range from 0.5 to 20 μm measured by laser granulometry.

7. The method according to claim 4, wherein said zinc-bearing compound is zinc oxide and wherein the detoxification agent is magnesium oxide.

8. The method according to claim 4, wherein the composition is micronized.

* * * * *